United States Patent [19]
Ressemann et al.

[11] Patent Number: 5,720,724
[45] Date of Patent: *Feb. 24, 1998

[54] INTRAVASCULAR CATHETER WITH DISTAL GUIDE WIRE LUMEN AND TRANSITION MEMBER

[75] Inventors: Thomas V. Ressemann, St. Cloud; Peter T. Keith, Fridley; Louis G. Ellis, St. Anthony, all of Minn.

[73] Assignee: SciMed Life Systems, Inc., Maple Grove, Minn.

[*] Notice: The term of this patent shall not extend beyond the expiration date of Pat. No. 5,658,251.

[21] Appl. No.: 710,966

[22] Filed: Sep. 24, 1996

Related U.S. Application Data

[63] Continuation of Ser. No. 439,959, May 12, 1995, which is a continuation of Ser. No. 197,169, Feb. 16, 1994, Pat. No. 5,425,711, which is a continuation of Ser. No. 833,099, Feb. 10, 1992, abandoned, which is a continuation-in-part of Ser. No. 796,901, Nov. 22, 1991, which is a continuation of Ser. No. 433,711, Nov. 13, 1989, abandoned, which is a continuation-in-part of Ser. No. 162,004, Feb. 29, 1988, Pat. No. 4,943,278, said Ser. No. 833,099, Feb. 10, 1992, is a continuation-in-part of Ser. No. 574,265, Aug. 28, 1990, Pat. No. 5,156,594.

[51] Int. Cl.$^6$ ................................................. A61M 29/00
[52] U.S. Cl. ...................................... 604/96; 606/194
[58] Field of Search ..................... 604/96–103, 280, 604/282; 600/18, 15, 16; 606/192–196

[56] References Cited

U.S. PATENT DOCUMENTS

| Re. 32,348 | 2/1987 | Pevsner | 128/325 |
|---|---|---|---|
| 2,225,762 | 12/1940 | Barnsteiner | 312/156 |
| 2,657,691 | 11/1953 | Nordstrom, Jr. | 128/303 |
| 2,687,131 | 8/1954 | Raiche | 128/349 |
| 2,912,981 | 11/1959 | Keough | 128/349 |
| 2,930,377 | 3/1960 | Cowley | 128/344 |
| 2,936,760 | 5/1960 | Gants | 128/349 |

(List continued on next page.)

FOREIGN PATENT DOCUMENTS

| 0 344 530 A1 | 12/1989 | European Pat. Off. |
|---|---|---|
| 0 368 523 A2 | 5/1990 | European Pat. Off. |
| 0 365 993 A1 | 5/1990 | European Pat. Off. |
| 0 416 734 A1 | 3/1991 | European Pat. Off. |
| 0 416 662 A2 | 3/1991 | European Pat. Off. |
| 0 441 384 A2 | 8/1991 | European Pat. Off. |

(List continued on next page.)

OTHER PUBLICATIONS

Paul G. Yock, U.S. patent application Ser. No. 852,197, filed Apr. 15, 1986, made public Jun. 7, 1988.

"Direct Balloon to Spring Tip Bond for Sleek Crossing", SciMed Life Systems, Inc., made public on date even with or prior to Sep. 9, 1996, 1 page.

Schneider (USA) Inc., brochure entitled *Monorail–Piccolino Coronary Balloon Dilatation Catheter*, Oct. 1988, 2 pages.

Advanced Cardiovascular Systems, Inc. *ACS RX Dilatation Catheters*, 1988, 2 pages.

Bjorn Nordenstrom, M.D., "New Instruments for Catheterization and Angiocardiography", *Radiology*, vol. 85, Jul.–Dec. 1965, pp. 256–259.

(List continued on next page.)

*Primary Examiner*—Corrine M. McDermott
*Attorney, Agent, or Firm*—Nawrocki, Rooney & Sivertson

[57] ABSTRACT

An over-the-wire balloon dilatation catheter of the short guide wire lumen type has a stainless steel hypotube catheter shaft section, a distal plastic shaft section attached to the hypotube and a balloon connected to the distal plastic shaft section. A relatively short guide wire lumen extends throughout the length of the balloon. The distal shaft section includes a reinforcing and kink-resistant transition member extending throughout the length of the distal shaft section. The transition member allows the proximal guide wire lumen aperture to be placed distally from the distal end of the hypotube. This configuration permits the length of the guide wire lumen to be minimized.

11 Claims, 2 Drawing Sheets

U.S. PATENT DOCUMENTS

| | | | |
|---|---|---|---|
| 3,225,762 | 12/1965 | Guttman | 128/214 |
| 3,976,720 | 8/1976 | Hammer et al. | 260/857 |
| 4,085,757 | 4/1978 | Pevsner | 128/325 |
| 4,137,906 | 2/1979 | Akiyama et al. | 128/2 A |
| 4,213,461 | 7/1980 | Pevsner | 128/348 |
| 4,261,339 | 4/1981 | Hanson et al. | 128/1 D |
| 4,289,128 | 9/1981 | Rusch | 128/207.15 |
| 4,311,146 | 1/1982 | Wonder | 128/325 |
| 4,323,071 | 4/1982 | Simpson et al. | 128/343 |
| 4,327,709 | 5/1982 | Hanson et al. | 128/1 D |
| 4,346,698 | 8/1982 | Hanson et al. | 128/1 D |
| 4,386,604 | 6/1983 | Hershey | 128/718 |
| 4,413,989 | 11/1983 | Schjeldahl et al. | 604/96 |
| 4,468,224 | 8/1984 | Enzmann et al. | 604/247 |
| 4,561,439 | 12/1985 | Bishop et al. | 128/348.1 |
| 4,582,181 | 4/1986 | Samson | 128/348.1 |
| 4,597,755 | 7/1986 | Samson et al. | 604/96 |
| 4,638,805 | 1/1987 | Powell | 128/344 |
| 4,652,258 | 3/1987 | Drach | 604/53 |
| 4,662,368 | 5/1987 | Hussein et al. | 128/303.1 |
| 4,705,507 | 11/1987 | Boyles | 604/101 |
| 4,721,117 | 1/1988 | Mar et al. | 128/772 |
| 4,748,982 | 6/1988 | Horzewski et al. | 128/344 |
| 4,762,129 | 8/1988 | Bonzel | 128/344 |
| 4,771,776 | 9/1988 | Powell et al. | 128/344 |
| 4,771,777 | 9/1988 | Horzewski et al. | 128/344 |
| 4,771,778 | 9/1988 | Mar | 123/344 |
| 4,771,782 | 9/1988 | Millar | 128/637 |
| 4,790,315 | 12/1988 | Mueller, Jr. et al. | 128/344 |
| 4,796,642 | 1/1989 | Harris | 128/772 |
| 4,798,193 | 1/1989 | Giesy et al. | 128/7 |
| 4,798,598 | 1/1989 | Bonello et al. | 604/280 |
| 4,811,743 | 3/1989 | Stevens | 128/772 |
| 4,820,349 | 4/1989 | Saab | 128/344 |
| 4,821,722 | 4/1989 | Miller et al. | 128/344 |
| 4,824,435 | 4/1989 | Giesy et al. | 604/49 |
| 4,838,268 | 6/1989 | Keith et al. | 128/344 |
| 4,846,174 | 7/1989 | Willard et al. | 128/344 |
| 4,850,358 | 7/1989 | Millar | 128/637 |
| 4,873,983 | 10/1989 | Winters | 128/657 |
| 4,877,031 | 10/1989 | Conway et al. | 128/344 |
| 4,881,547 | 11/1989 | Danforth | 128/344 |
| 4,896,670 | 1/1990 | Crittenden | 606/194 |
| 4,906,241 | 3/1990 | Noddin et al. | 606/194 |
| 4,917,088 | 4/1990 | Crittenden | 606/194 |
| 4,921,478 | 5/1990 | Solano et al. | 604/53 |
| 4,928,693 | 5/1990 | Goodin et al. | 128/637 |
| 4,932,413 | 6/1990 | Shockey et al. | 128/657 |
| 4,940,062 | 7/1990 | Hampton et al. | 128/772 |
| 4,943,278 | 7/1990 | Euteneuer et al. | 604/96 |
| 4,944,745 | 7/1990 | Sogard et al. | 606/194 |
| 4,946,466 | 8/1990 | Pinchuk et al. | 606/194 |
| 4,947,864 | 8/1990 | Shockey et al. | 128/772 |
| 4,953,553 | 9/1990 | Tremulis | 128/637 |
| 4,964,409 | 10/1990 | Tremulis | 128/657 |
| 4,966,148 | 10/1990 | Millar | 128/637 |
| 4,976,720 | 12/1990 | Machold et al. | 606/194 |
| 4,988,356 | 1/1991 | Crittenden et al. | 606/192 |
| 4,994,032 | 2/1991 | Sugiyama et al. | 604/96 |
| 4,998,917 | 3/1991 | Gaiser et al. | 604/96 |
| 4,998,923 | 3/1991 | Samson et al. | 606/194 |
| 5,002,532 | 3/1991 | Gaiser et al. | 604/101 |
| 5,003,990 | 4/1991 | Osypka | 128/772 |
| 5,024,234 | 6/1991 | Leary et al. | 128/663.01 |
| 5,032,113 | 7/1991 | Burns | 604/96 |
| 5,034,001 | 7/1991 | Garrison et al. | 604/53 |
| 5,035,686 | 7/1991 | Crittenden et al. | 604/96 |
| 5,035,705 | 7/1991 | Burns | 606/194 |
| 5,040,548 | 8/1991 | Yock | 128/898 |
| 5,042,985 | 8/1991 | Elliot et al. | 606/192 |
| 5,047,045 | 9/1991 | Arney et al. | 606/194 |
| 5,050,606 | 9/1991 | Tremulis | 128/637 |
| 5,057,120 | 10/1991 | Farcot | 606/194 |
| 5,061,273 | 10/1991 | Yock | 606/194 |
| 5,061,738 | 10/1991 | Solomon et al. | 523/100 |
| 5,102,403 | 4/1992 | Alt | 604/280 |
| 5,131,407 | 7/1992 | Ischinger et al. | 128/772 |
| 5,135,535 | 8/1992 | Kramer | 606/194 |
| 5,154,725 | 10/1992 | Leopold | 606/194 |
| 5,156,594 | 10/1992 | Keith | 604/96 |
| 5,159,937 | 11/1992 | Tremulis | 128/772 |
| 5,180,367 | 1/1993 | Kontos et al. | 604/101 |
| 5,425,711 | 6/1995 | Ressemann et al. | 604/96 |

FOREIGN PATENT DOCUMENTS

| | | |
|---|---|---|
| 0 479 730 A1 | 4/1992 | European Pat. Off. . |
| 0 332 649 B1 | 2/1993 | European Pat. Off. . |
| 0 282 143 B1 | 9/1993 | European Pat. Off. . |
| 591963 | 5/1924 | France . |
| 627828 | 10/1978 | U.S.S.R. . |
| 1251 914 A | 8/1986 | U.S.S.R. . |
| 2 078 114 A | 1/1982 | United Kingdom . |
| WO86/06285 | 11/1986 | WIPO . |
| WO88/00844 | 2/1988 | WIPO . |
| WO92/00775 | 1/1992 | WIPO . |

OTHER PUBLICATIONS

Declaration of Paul G. Yock, M.D., in Support of ACS's Opposition to Schneider's Motion for Preliminary Injunction, dated Nov. 27, 1989, filed Dec. 4, 1989, in Schneider (Europe) AG v. Advanced Cardiovascular Systems, Inc., No. C88-20742-WAI, United States District Court, Northern District of California (including Exhibits 1–7) made public on or date even with or prior to Sep. 24, 1996.

Exhibit 1 to Yock Declaration dated Dec. 4, 1989: Curriculum Vitae of Paul G. Yock, M.D., 5 pages.

Exhibit 2 to Yock Declaration dated Dec. 4, 1989: Written Description entitled "Single–Operator Angioplasty System", 5 pages.

Exhibit 3 to Yock Declaration dated Dec. 4, 1989: Copy of Slide Comparing the ACS RX® with the Original Schneider Monorail®, 1 page.

Exhibit 4 to Yock Declaration dated Dec. 4, 1989: Ronald E. Vlietstra, M.B., Ch. B. et al., article entitled "PTCA Percutaneous Transluminal Coronary Angioplasty", 2 pages. Roger F.J. Shepherd, M.B., B. Ch. et al., article entitled The History of Balloon Angioplasty, 3 pages.

Exhibit 5 to Yock Declaration dated Dec. 4, 1989: L.E. Afzelius et al., *Lakartidningen*, article entitled "Ballongdilatation Av Esofagusstrikturer En Ny Behandlingsmetod", vol. 79, No. 30–31 (1982), 3 pages, and English translation, 13 pages.

Exhibit 6 to Yock Declaration dated Dec. 4, 1989: Albert A. Moss, M.D. et al., *NMR, CT, and Interventional Radiology*, article entitled "Interventional Gastrointestinal Procedures", 8 pages.

Exhibit 7 to Yock Declaration dated Dec. 4, 1989: Copy of U.S. Patent No. 3,884,242 entitled "Catheter Assembly" in the name of Bazell et al., 11 pages.

Bjorn Nordenstrom, *Balloon Catheters For Percutaneous Insertion Into The Vascular System*, Department of Diagnostic Roentgenology, Karolinska Sjukhuset, Stockholm, Sweden, Mar. 2, 1962, pp. 411–416.

"USCI Lo Profile II Balloon Dilatation Catheters," C.R. Bard, Inc. 1987, 4 pages.

"Until someone does it, no one thinks it can be done," C.R. Bard, Inc. 1988, 4 pages.

The Ace, "Fixed–Wire Technology, Perfected", SCIMED Life Systems, Inc., made public on date even with or prior to Sep. 24, 1996, 4 pages.

The illustration labeled "Ace Corewire" is a detailed drawing of a corewire for use with the ACE catheter, made public on a date even with or prior to Sep. 24, 1996.

FIGS. 6–8 of U.S. patent application, Ser. No. 07/806,588, filed on Dec. 12, 1991, device shown in figures made public on date even with or prior to Sep. 24, 1996.

Press Release dated Aug. 28, 1989, SciMed Life Systems, Inc., 1 page.

Press Release dated Sep. 18, 1989, Schneider (USA), 1 page.

Press Release dated May 23, 1990, Schneider, 1 page.

Schneider, brochure entitled *The Monorail Piccolino*, made public on date even with or prior to Sep. 24, 1996, 4 pages.

Schneider, *Monorail System* instruction manual, made public on date even with or prior to Sep. 24, 1996, 7 pages.

Schneider–Shiley AG, *Monorail–Bonzel Coronary Dilatation System*, made public on date even with or prior to Sep. 24, 1996, 8 pages.

SciMed Life Systems, Inc. "Case Study: Ace Conformability Steerability", 1989, 1 page.

SciMed Life Systems, Inc. "Unibody Core Wire for Excellent Tip Response", 1 page.

Overlie et al., "Advances in Balloon Catheter Technology: Expanding Clinical Efficacy", SciMed Life Systems, Inc. 1989, 4 pages.

Declaration of Peter T. Keith including Exhibits A–D dated Feb. 3, 1997, 14 pages.

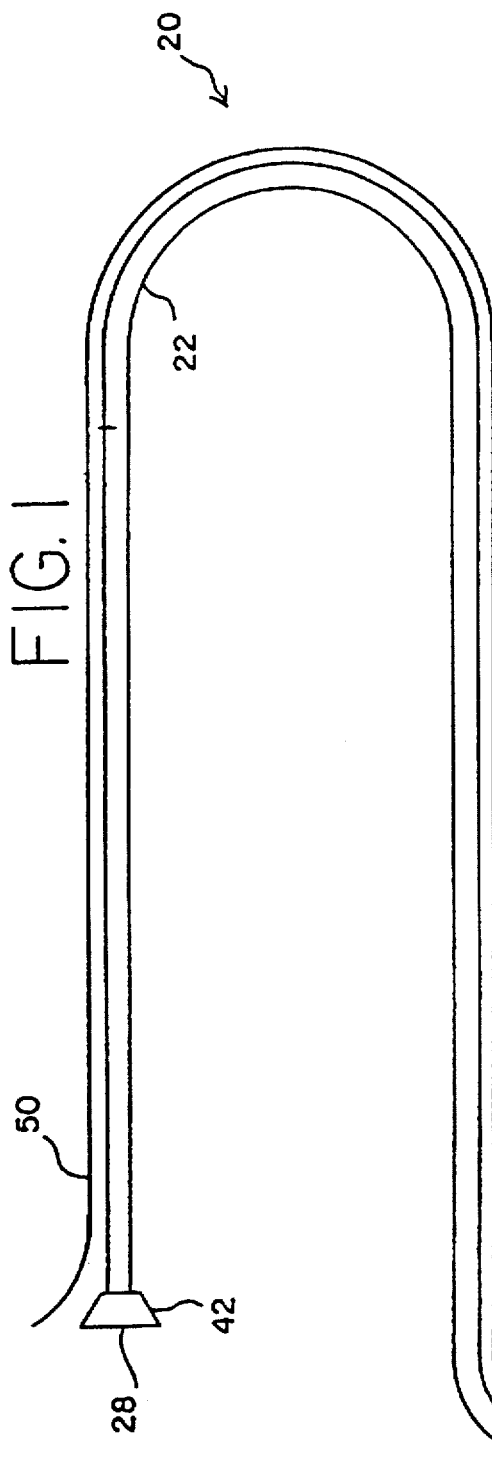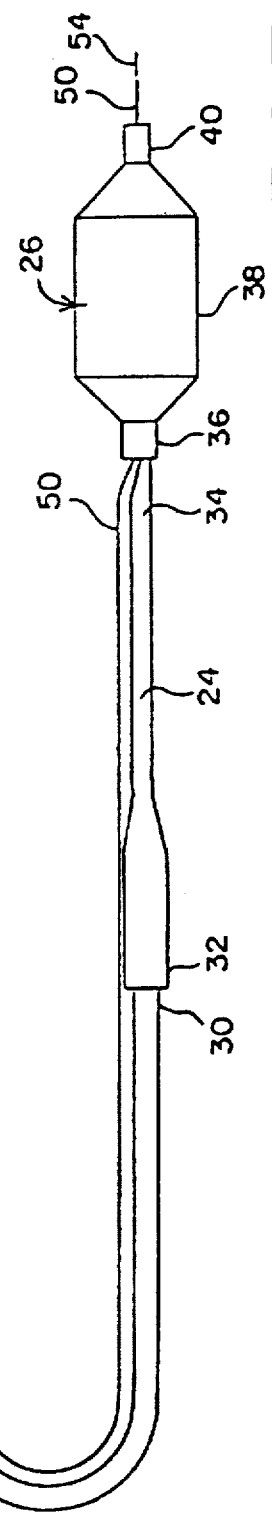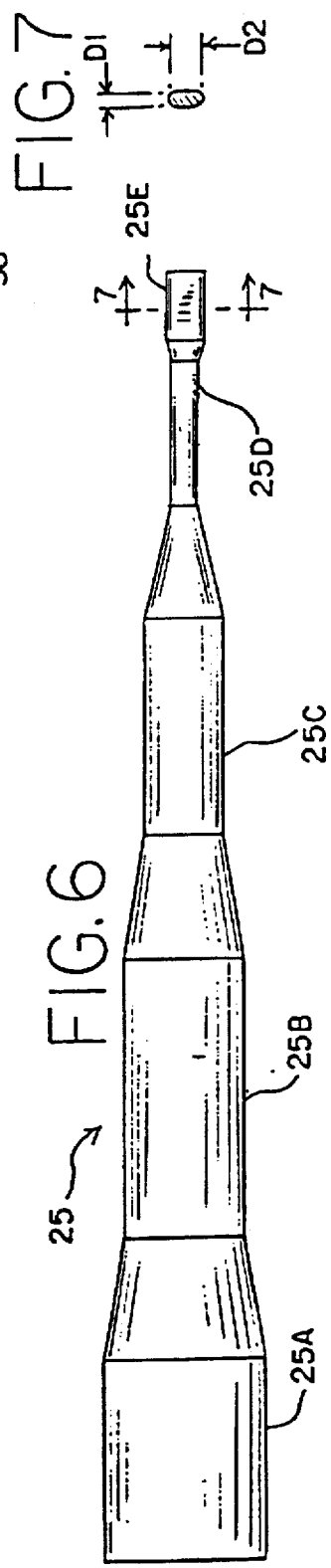

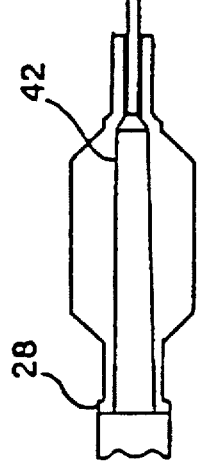
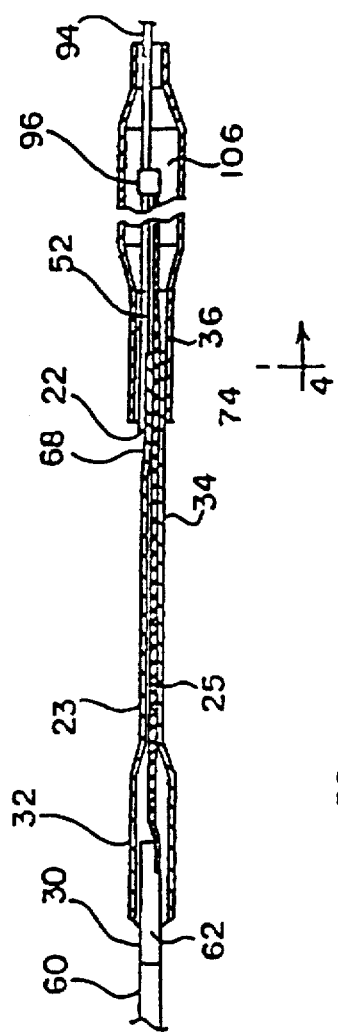
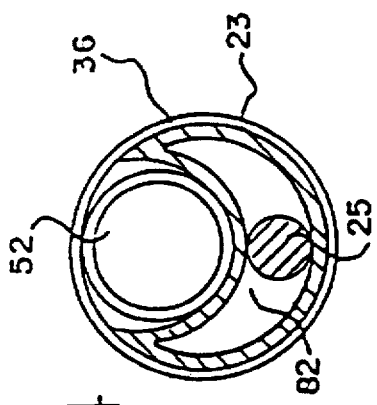
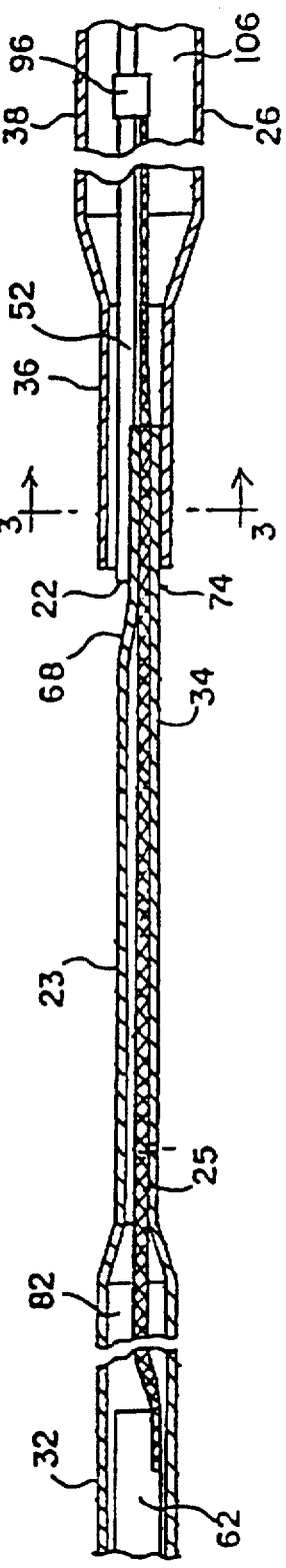

INTRAVASCULAR CATHETER WITH DISTAL GUIDE WIRE LUMEN AND TRANSITION MEMBER

RELATED APPLICATIONS

This application is a continuation of co-pending application Ser. No. 08/439,959, filed May 12, 1995 which is a continuation of application Ser. No. 08/197,169, filed Feb. 16, 1994, now U.S. Pat. No. 5,425,711 which is a continuation of application Ser. No. 07/833,099, filed Feb. 10, 1992, now abandoned which is a continuation-in-part of two applications; Ser. No. 07/796,901, filed Nov. 22, 1991 which is a continuation of application Ser. No. 07/433,711, filed Nov. 13, 1989 now abandoned, which is a continuation-in-part of application Ser. No. 07/162,004, filed Feb. 29, 1988, now issued as U.S. Pat. No. 4,943,278; said application Ser. No. 07/833,099, filed Feb. 10, 1992 is a continuation-in-part of application Ser. No. 07/574,265, filed Aug. 28, 1990, now issued as U.S. Pat. No. 5,156,594.

BACKGROUND OF THE INVENTION

The present invention relates to an intravascular catheter. In particular, the present invention relates to an intravascular catheter, such as a dilatation balloon catheter, of the type which is advanced over a guide wire having a distal guide wire lumen which is shorter than the length of the catheter and which extends through the balloon of the catheter.

Angioplasty procedures have gained wide acceptance in recent years as efficient and effective methods for treating types of vascular disease. In particular, angioplasty is widely used for opening stenoses in the coronary arteries, although it is also used for the treatment of stenoses in other parts of the vascular system.

The most widely used form of angioplasty makes use of a dilatation catheter which has an inflatable balloon at its distal end. Typically, in coronary procedures a hollow guide catheter is used in guiding the dilatation catheter through the vascular system to a position near the stenosis (e.g., to the coronary artery ostia). Using fluoroscopy, the physician guides the dilatation catheter the remaining distance through the vascular system until a balloon is positioned to cross the stenosis. The balloon is then inflated by supplying fluid under pressure, through an inflation lumen in the catheter, to the balloon. The inflation of the balloon causes a widening of the lumen of the artery to. reestablish acceptable blood flow through the artery. In procedures in the peripheral vessels (vessels other than coronary vessels) the guide catheter may not always be used.

Preferably a catheter will have several physical characteristics. First, there has been a continuing effort to reduce the profile and shaft size of the dilatation catheter so that the catheter not only can reach but also can cross a very tight stenosis. Portions of dilatation catheter must also be sufficiently flexible to pass through tight curvatures especially in the coronary arteries. The ability of a catheter to bend and advance through the vasculature is commonly referenced to as the "trackability of the catheter." A further requirement of a dilatation catheter is its "pushability." This involves the transmission of longitudinal forces along the catheter from its proximal end to its distal end so that a physician can push the catheter through the vascular system and the stenoses. The catheter should be both relatively trackable and pushable.

Two commonly used types of dilatation catheters are referred to as "over-the-wire" catheters and "non-over-the-wire" catheters. An over-the-wire catheter is one in which a separate guide wire lumen is provided in the catheter so that a guide wire can be used to establish the path through the stenoses. The dilatation catheter can then be advanced over the guide wire until the balloon on the catheter is positioned within the stenosis.

In some over-the-wire catheters, the guide wire lumen does not extend the entire length of the catheter. In this type of catheter, the guide wire lumen extends only from the distal end of the balloon to a point proximal of the balloon but distal of the proximal end of the catheter.

It is sometimes desirable to use a smaller or larger balloon than that initially used. The catheter is preferably exchanged by leaving the guide wire in place and using it as a guide for the next catheter. It is said that shortened guide wire lumen type catheters are easier to exchange than catheters having the guide wire lumen extending the entire length of the catheter.

While several structures for shortened guide wire lumen dilatation catheters have been proposed, these structures suffer from several disadvantages. For example, some catheters have relatively flexible one-piece plastic design. Because the distal end of the guide wire exits the catheter near the distal end of the shaft portion, the guide wire cannot contribute to the pushability of the majority of the shaft portion. Thus, the proximal shaft portion of such catheters has low column strength. With such a configuration, the catheter shaft and the portion of the guide wire which extends outside of the guide wire lumen will tend to separate toward opposite walls of the artery as the catheter is advanced or retracted. That is, the shafts and guide wire tend to "scissor" and bow, buckle and the shaft may even kink when the balloon is advanced or retracted across a lesion. This scissoring or bowing may lead to abrasions to the inner lining of the artery. This scissoring or bowing also leads to poor pushability and trackability of the catheter. To counteract this deficiency, some known designs have extended the length of the guide wire lumen and/or provided additional stiffener elements in the shaft.

In one recently developed design, a large part of the proximal catheter shaft is made of a metallic tube (commonly referred to as a hypotube). As described in more detail below, the hypotube construction provides the desired pushability and yet may have a relatively small outer diameter or profile.

In catheters of this hypotube design, the inlet for the guide wire lumen is usually placed near or adjacent to the distal end of the hypotube. (The "inlet" to the guide wire lumen, here refers to the proximal guide wire lumen aperture and the "outlet" to the guide wire lumen refers to the distal guide wire lumen aperture.) This location of the guide wire inlet, however, may not always be at a location which is the most desirable. If the guide wire inlet is placed adjacent the distal end of the hypotube, either the flexible plastic shaft segment will be short or the guide wire lumen will be relatively long.

On the other hand, placing the guide wire lumen inlet distally of the distal end of the hypotube (in the plastic shaft segment) has several disadvantages with presently available designs. The hypotube is relatively stiff and the plastic segment is relatively flexible. The part of the plastic shaft segment through which the guide wire runs will also be relatively stiff when the guide wire is in place (compared to the part of the plastic segment through which the guide wire does not run). Thus, if the guide wire inlet is placed distally of the distal end of the hypotube, a relatively flexible section is defined between two relatively stiff sections. Such a configuration will tend to bend or buckle in the relatively flexible area as an attempt is made to advance the catheter through the vasculature. Therefore, the responsiveness of the catheter will be substantially diminished. Further, the catheter might tend to kink at the section between the two relatively stiff sections. Such kinking would tend to close the inflation lumen—an obviously undesirable event.

Therefore, it is an object of the present invention to provide an over-the-wire catheter of the short guide wire lumen type having improved pushability and trackability.

SUMMARY OF THE INVENTION

The present invention is an intravascular catheter which may be guided over a guide wire, such as a dilation balloon catheter, having a relatively stiff proximal shaft section and a relatively flexible distal shaft section. The guide wire lumen extends from a distal end of the catheter through a balloon of the catheter and exits the catheter at a point proximal of the balloon. The distal shaft section is reinforced, by a transition member, in a manner that provides a relatively flexible distal end and yet prevents closure or kinking in the flexible part of the catheter. The transition member permits the inlet to the guide wire lumen to be placed distally of the end of the relatively stiff catheter shaft, that is, in the more flexible section.

In one embodiment of the present invention, the catheter is a balloon dilatation catheter which includes a proximal shaft section defined by a thin-walled, high strength metallic tube. A distal shaft section is attached to the distal end of the metallic tube. The balloon is attached to the distal end of the distal shaft section. An inflation lumen is defined through the metallic shaft section and the distal shaft section. Inflation pressure is provided to the balloon through the inflation lumen. A lumen which receives a guide wire extends at least the length of the balloon. The guide wire lumen inlet is disposed distally of the distal end of the metallic tube. The distal shaft section includes a transition member which gives the distal shaft section axial rigidity.

The transition member advantageously permits placement of the proximal guide wire lumen opening near the proximal end of the balloon while optimizing pushability/trackability in the flexible distal shaft section. The transition member also prevents kinking of the inflation lumen which may occur due to the abrupt change from the relatively stiff metallic tube to the relatively flexible distal shaft section.

BRIEF DESCRIPTION OF THE DRAWINGS

FIG. 1 is a sectional side elevational view of a preferred embodiment of a balloon dilatation catheter of the present invention having a distal guide wire lumen therethrough and showing a guide wire.

FIG. 2 is a sectional side elevational view of the proximal end of the balloon dilatation catheter of FIG. 1.

FIG. 3 is an enlarged sectional side elevational view of the distal end of the balloon dilatation catheter of FIG. 1.

FIG. 4 is an enlarged sectional view as taken along line 4—4 in FIG. 2.

FIG. 5 is an enlarged sectional side elevational view of a portion of the balloon dilatation catheter of the FIG. 1.

FIG. 6 is a side view of a preferred embodiment of the transition member of the present invention.

FIG. 7 is a sectional view as taken along line 7—7 in FIG. 6.

Although the above-identified figures set forth one embodiment of the invention, other embodiments are also contemplated. This disclosure presents an illustrated embodiment of the present invention by way of representation and not limitation. It should be understood that numerous modifications and embodiments can be devised by those skilled in the art which will fall within the scope and spirit of the principles of this invention.

DETAILED DESCRIPTION OF THE PRESENTLY PREFERRED EMBODIMENTS

Overall Catheter Structure

A balloon dilatation catheter 20 covering one embodiment of the present invention is illustrated generally in FIG. 1. Although the following description of the invention is directed to a balloon dilation catheter, it will be appreciated by those skilled in the art that the invention may be used on other interventional catheters with vascular interoperative devices, such as atherectomy devices, ultrasonic imaging and therapeutic catheters, laser catheters, stent delivery catheters, and perfusion catheters.

In the embodiment of FIG. 1, the catheter 20 has a proximal main shaft section 22, a distal shaft section 24 and a balloon 26. The main shaft section 22 has a proximal end 28 and a distal end 30. Likewise, the distal shaft section 24 has a proximal end 32 and a distal end 34. The balloon 26 has a proximal neck or waist 36, an intermediate expandable section 38 and a distal neck or waist 40.

As illustrated in FIG. 1, the distal end 30 of the main shaft section 22 is connected to the proximal end 32 of the distal shaft section 24, and the distal end 34 of the distal shaft section 24 is connected to the proximal neck 36 of the balloon 26. In use, the catheter 20 is coupled to an inflation device (not shown) by a manifold 42, such as a luer manifold. The manifold 42 is connected to the proximal end 28 of the main shaft section 22. The inflation device provides or removes inflation solution from the catheter 20 to selectably inflate or deflate the intermediate expandable segment 38 of the balloon 26 (in FIG. 1, expandable segment 38 is shown in its inflated configuration).

The catheter 20 of the present invention is designed for use in combination with a catheter guide element such as a guide wire 50. In use in a coronary application, both the guide wire 50 and the catheter 20 are fed through and guided to an arterial lesion by means of a tubular guide catheter (not shown). Both the catheter 20 and the guide wire 50 are longer than the guide catheter, with a typical catheter length of approximately 135 cm and a typical guide wire length of approximately 175 cm. As illustrated in FIG. 1, the guide wire 50 extends longitudinally along the exterior of the main shaft section 22 and the distal shaft section 24 of the catheter 20.

Adjacent the distal end 34 of the distal shaft section 24, the guide wire 50 enters a lumen 52 in the catheter 20 through a first proximal aperture or inlet 22 at the proximal neck 36 of the balloon 26. The lumen 52 extends distally through the balloon until it exits the balloon 26 through a second distal aperture or outlet 94 at the distal neck section 40. As seen in FIG. 2, the guide wire lumen 52 provided through the balloon section 26 is relatively short compared to the overall length of the catheter 20. The guide wire 50 is only entrained in the catheter 20 through this guide wire lumen 52.

In this embodiment, the guide wire lumen 52 is approximately equal to the length of the balloon 26, although it is contemplated that the lumen 52 may be longer. For example, the guide wire inlet 22 may be positioned more proximally in the distal shaft section 24. It is believed that the guide wire inlet 22 may be placed about 5 cm. distally of the distal end of the main shaft section 22 and still having improved performance characteristics over presently available catheters.

The guide wire 50 has a proximal end 53 and a distal end 54 and is of a typical structure for guiding angioplasty catheters. At its distal end 54, the guide wire 50 preferably has a coil and rounded tip structure which is bendable for steerability of the guide wire.

Referring now to FIG. 2, which shows the distal end of the catheter 20 in greater detail, it is seen that the proximal end 28 of the main shaft section 22 has a strain relief tube 60 disposed between the luer manifold 42 and main shaft section 22. The strain relief tube 60 is larger than the main shaft section 22, and thus provides a step-wise strain relief function between the relatively inflexible luer manifold 42 and the more flexible main shaft section 22. The main shaft section 22, strain relief tube 60 and luer manifold 42 are secured together respectively by suitable adhesive bonding means such as LOCTITE 405 available from Loctite Corp. (Newington, Conn.) OR UV MASTERBOND 4000 available from Masterbond (Hackensack, N.J.), or a urethane such as Prototype No. TL-03341 available from H. B. Fuller (St. Paul, Minn.), and Tracon BA 2135D, available from Tracon (Medford, Mass).

In an exemplary embodiment, the total workable length of the catheter 20 is approximately 135 cm. The preferred workable length of the main shaft 22 is approximately 106 cm. (the total length of the main shaft 22 is 112 cm. including the part which typically is in the manifold 42).

Referring now to FIG. 4, the tubular shaft 23 of distal shaft section 24 is tapered from a relatively larger proximal end 32 to a smaller distal end 34. The length of the balloon 26 may be approximately between 20–50 mm. The length of the guide wire lumen 52 is preferably in the range from 3.5 to 7 cm.

The Main Shaft Section

The proximal main shaft section 22 is a relatively stiff tubular shaft. Preferably, the main shaft section 22 is formed as a thin-walled, high strength stainless steel tube structure, which is commonly referred to as hypodermic tubing or hypotube. A suitable hypotube has a nominal O.D. of approximately 0.023 in. and a nominal I.D. of approximately 0.017 in. The main shaft section 22 is provided with a lubricous coating (such as polytetrafluoroethylene) to reduce frictional resistance. A suitable coating thickness is about 0.0005 in. As a tubular structure, the interior of the main shaft section 22 is substantially hollow, and thus defines an inflation lumen 62 extending from the proximal end 28 to the distal end 30. The inflation lumen 62 provides a path through which inflation fluid is provided to and from the balloon 26.

The thin-walled metallic tube structure of the main shaft section 22 is stiff enough to provide the desired pushability yet allows for a relatively small profile shaft at the proximal end of the catheter. The inherent high strength nature of the metallic tube also allows it to withstand the fluid pressure necessary for proper catheter operation.

The high column strength and thickness of a hypotube shaft also gives the catheter improved responsiveness. That is, the balloon and the distal regions of the catheter move more definitely (in a 1:1 relationship) with motions imparted at the catheter's proximal end by a physician to actually "sense" the pathway as the catheter is tracked. This improved responsiveness gives valuable information to the physician regarding the passage of the catheter to and through the lesions. The catheter is, thus, extremely responsive to a doctor's controlling movement of the catheter from its proximal end, while at the same time having a relatively small profile and enhancing catheter visualization via fluoroscopy.

It will be recognized by those skilled in the art that other relatively stiff materials may be used for the main catheter shaft section 22. For example, a braided polyimide or other relatively rigid composite material may be used.

Catheter Distal Shaft Section

The distal shaft section 24 extends distally from the main shaft section 22 to the balloon neck 36. The distal shaft section 24 includes a tubular shaft 23 and a transition member 25. The tubular shaft 23 is more flexible than the main shaft section 22. In an exemplary embodiment, the tubular shaft 23 is a thermoplastic, such as high density polyethylene (HDPE). Such a tubular section may be formed by extrusion with thermal mechanical drawing to form the necked section. The interior of the tubular shaft 23 is also substantially hollow and defines an inflation lumen 82 extending from the proximal end 32 to the distal end 34. HDPE is preferred since it is relatively lubricous. The lubricity may be further enhanced by coating the outer surface of the shaft and/or the inner surface of the guide wire lumen with silicone.

The proximal end 32 of the distal shaft 23 extends over the distal end 30 of the main shaft section 22 and is attached thereto by a suitable bond such as a cyanoacrylate adhesive. As best seen in FIG. 3, the inflation lumen 62 of the main tube section 22 is connected with the inflation lumen 82 of the distal shaft section 24. The tubular shaft 23 of the distal shaft section 24 is bonded at its distal end to the neck 36 of the balloon member 26 at bonding region 74. The tubular shaft 23 may be bonded to the balloon 26 by means of urethane adhesive such as No. UR3507 available from H. B. Fuller (St. Paul, Minn.).

The distal shaft 24 is tapered distally from its relatively larger proximal end 32 to its thinner distal end 34. In an exemplary embodiment, the larger proximal end 32 of the shaft section 23 is approximately 2 cm long (measured from the end of the distal end of the main shaft segment 22 to the taper) and has a nominal O.D. of approximately 0.031 in. and a nominal I.D. of approximately 0.026 in. The smaller distal end 24 is approximately 30 cm. long (measured from the taper to the proximal end of balloon neck 36) and has a nominal O.D. of approximately 0.026 in. and a nominal I.D. of approximately 0.021 in.

An aperture defined by a crimp 68 in the tubular shaft 23 is provided at the distal end 34 of the distal shaft section 24. The crimp 68 defines the guide wire inlet 22 for the catheter 20. The crimp 68 extends from its proximal origin adjacent the balloon neck 36 to its greatest lateral depth in the bonding region 74. The crimp 68, as further illustrated in FIG. 3, does not seal off or close the inflation lumen 82, but transforms the inflation lumen 82 from a circular cross-section to a relatively crescent shape cross-section. It will be recognized by those skilled in the art that other configurations for the guide wire inlet are possible.

One preferred method of making the crimp 68 in the tubing for the plastic (preferably HDPE) distal shaft section 24 uses a forming blade and die arrangement. The forming blade has a crescent-shaped tip which is used to form the crescent-shaped crimp 68. The tubing is first loaded into the die which snugly envelopes most of the tube except for an opening for the blade. The tubular shaft is then pressurized, for example to 120 p.s.i. The blade is then forced onto the tubing to cold form the HDPE. The blade and die assembly is then dipped in a heated water bath, for example at 90° C. for about three minutes. The assembly is then removed and dipped in cooler water, for example water at room temperature or cooler for about 1 minute. The tubing is then removed from the assembly and trimmed to the desired length.

The transition member provides two related functions. First, it provides axial or column strength to the distal shaft section 24. Second, it prevents kinking of the distal shaft section 24. As discussed above, the hypotube section 22 is relatively stiff and the distal shaft section 23 is relatively flexible. Further, with the guide wire 50 in the guide wire lumen 52, relatively stiff sections are defined at both ends of the distal shaft section 24. Without the transition member 25, such a configuration will tend to bend or buckle in the relatively flexible area as an attempt is made to advance the catheter 20 through the vasculature. The responsiveness of the catheter would thus be substantially diminished. Further, the catheter 20 might tend to kink at the transition section.

The transition member 25 is a structural member which increases the stiffness of the distal shaft section 24. The transition member 25 is less stiff (or has less axial strength) than the hypotube of the main shaft section 22 but is more stiff than the distal shaft 23. The transition member, however, is configured to be more trackable than the main shaft section 22. Thus, the pushability of the distal shaft section 24 will preferably be more pushable than the distal shaft 23 and yet be more trackable than the main shaft section 22.

In the preferred embodiment, the transition member 25 comprises a solid core ware which is attached at its proximal end to the hypotube 22 by brazing or other suitable means and to the guide wire lumen 52 and marker band 96 at its distal end by adhesive bonding or other suitable means. In one preferred method for bonding the core wire 25 to the guide wire lumen 52 and marker band 96, the wire is suspended by means of a magnetic field such that it is centered in on the bottom side of the outer surface of the guide wire lumen 25. The magnetic field is such that the core wire is at equilibrium when it is centered. Once the core wire is positioned and aligned with the marker band 96, the bond is made.

The core wire 25 preferably provides varying flexibility along its length such that its flexibility increases in the distal direction. As illustrated best in FIG. 6 (not shown to scale), this may be accomplished by having a core wire with one or more ground tapers. In an exemplary embodiment, the core wire 25 is made of V304 stainless steel and manufactured by centerless grinding. The core wire 25 preferably has four main sections, 25A, 25B, 25C and 25D and a distal bonding section 25E. The core wire 15 is preferably stress relieved by exposing the wires before grinding to a temperature in a range of from 500° F. to 800° F. for a time period from about 30 min. to about 6 hours, and preferably at 750° F. for about 5 hours including ramp-up time. The first proximal section 25A is approximately 1.25 in. long and has a diameter of approximately 0.012 in. The second middle section 25B is approximately 4 in. long and has a diameter of about 0.0095 in. The third section 25C is approximately 4.6 in. long and has a diameter of about 0.0070. The fourth section 25E is preferably approximately 0.125 in. long and has a diameter of approximately 0.0030 in. The fourth section 25E of the core wire 25 provides a smooth transition from the stiffness of the core wire to the stiffness of the combination of the balloon 26 and guide wire 50. As illustrated in FIG. 7, the most distal section 25E is flattened to facilitate bonding. The preferred dimensions for D1 and D2 are 0.0014 in. and 0.0040 in., respectively and the preferred length is about 0.051 in.

In this embodiment, the length of the distal shaft section 24 (from the end of the hypotube 22 to approximately the guide wire lumen opening) is about 29 cm. It will be recognized that this length may vary depending on the other dimensions of the catheter as well as the intended use. For example, the length of the distal shaft section 24 is preferably in a range from about 25 cm to about 40 cm. It will be appreciated that the dimensions and configurations of the core wire 25 will vary depending on the length of the distal shaft section 24.

Catheter Balloon

The balloon 26 extends distally from the distal shaft section 24 and is bonded thereto adjacent the bonding region 74. A suitable balloon material is a polyolefin which has been treated by radiation cross linking. The balloon 26 may also be silicone coated. A suitable polyolefin is available from E. I. DuPont Nemours & Co. (Wilmington, Del.) under the tradename SURYLYN® Ionomer.

The balloon 26 includes the guide wire lumen 52 extending through its entire length. The guide wire lumen 52 is preferably formed from thin-walled high density polyethylene. In an exemplary embodiment, the tube for the guide wire lumen is approximately 3.5 cm. long and has a nominal O.D. of approximately 0.021 in. and a nominal I.D. of approximately 0.016 in.

The distal open end 94 of the guide wire lumen 52 provides an outlet at the distal neck portion 40 of the balloon 26, and the proximal open end 22 of the guide wire lumen provides an inlet at the proximal neck portion 36 of the balloon 26. The guide wire lumen 52 is bonded to the balloon 26 at the distal neck 40 and the proximal neck 36. A suitable bonding material for bonding the guide wire lumen 52 to the balloon section 26 is urethane adhesive, such as a urethane available as No. UR3507 available from H. B. Fuller (St. Paul, Minn.).

At least one band marker 96 is provided about the guide wire lumen (preferably centered within the expandable segment 38 of the distal balloon section 26) to aid in determining the position of the catheter 20 via fluoroscopy during an angioplasty procedure.

The distal end 34 of the shaft 23 of the transition section 24 is also bonded by a urethane, such as No. UR3507 available from H. B. Fuller (St. Paul, Minn.) to the opening of the proximal neck portion 36 in an area immediately adjacent to the guide wire lumen 52. The distal end 34 and the guide wire lumen 52 are bonded to the proximal neck 36 in such a manner that the inflation lumen 82 of the distal shaft section 24 is in fluid communication with the interior 106 of the balloon 26, while at the same time, the interior of the balloon 26 is sealed off from the atmosphere. As illustrated best in FIG. 3, the guide wire lumen 52 is thus affixed to the proximal neck 36 in an "off axis" alignment.

Preferably, some of the plastic parts of the catheter are plasma treated to increase their bonding characteristics. For example, the outer surface of the guide wire tube, the HDPE distal shaft, the manifold, and the strain relief between the manifold and hypotube may be plasma treated using helium or oxygen plasma treating techniques.

The present invention is described above with reference to a dilatation balloon as the means for reducing the stenosis. Other stenosis reducing mechanisms may also be used. For example, the device for reducing or ablating the stenosis may be an atherectomy-type cutter, a laser device, a water jet device and sonic or ultrasonic therapeutic devices. The present invention may also be used with other interoperative devices such as drug delivery devices, ultrasonic imaging devices, and perfusion devices.

Conclusion

The transition member, such as core wire 25, (particularly one with a tapered design) allows the proximal guide wire opening 22 to be placed near the proximal neck 36 of the balloon 26. In the present embodiment, the guide wire lumen 52 extends only through the balloon 26, and thus the length of the guide wire lumen 52 is approximately equal to the length of the balloon 26 (preferably about three centimeters).

The core wire 25 creates an intermediate stiffener element between the relatively stiff main shaft section 22 and the relatively flexible tubular shaft 23 of distal shaft section 24 to optimize tracking and pushing.

The balloon dilatation catheter of the present invention is an over-the-wire catheter structure with a distal guide wire lumen which optimizes the performance of such a catheter in a way not previously considered or achieved. The use of a hypotube-type main shaft for the catheter allows the attainment of a high strength, pushable shaft having thin walls and small diameter.

The reinforcing and kink-resistant tapered core wire allows the proximal guide wire lumen inlet to be placed distally from the end of the main shaft section and near the proximal end of the balloon. The core wire also provides a more gradual transition between the relatively stiff main catheter shaft and the relatively flexible distal section of the catheter shaft. The distal shaft section 24 has good pushability while still being very trackable.

Although the present invention has been described with reference to preferred embodiments, workers skilled in the art will recognize that changes may be made in form and detail without departing from the spirit and scope of the invention.

We claim:

1. An intravascular catheter assembly comprising:

a proximal shaft segment having a proximal end, a distal end, and a single lumen defined therethrough which extends substantially from the proximal end to the distal end;

a balloon;

a distal shaft segment connected between the distal end of the proximal shaft segment and the balloon, the distal shaft segment being more flexible than the proximal shaft segment; the distal shaft segment having an inflation lumen defined therethrough wherein the inflation lumen of the distal shaft segment and the single lumen of the proximal shaft segment are in fluid communication with one another to provide inflation pressure to the balloon;

a transition member secured to the proximal shaft segment and extending distally into the distal shaft segment, the transition member being less rigid than the proximal shaft segment;

a guide wire tube defining a guide wire lumen therethrough extending from a location proximal of the balloon to a location distal of the balloon;

a guide wire lumen inlet spaced distally from the distal end of the proximal shaft segment and communicating between the guide wire lumen and outside of the catheter; and a guide wire, the guide wire being inserted through the guide wire tube and guide wire lumen inlet.

2. An intravascular catheter assembly according to claim 1 wherein the proximal shaft segment is defined by a metallic tube.

3. An intravascular catheter assembly according to claim 1 wherein the distal shaft segment is made from a plastic material.

4. An intravascular catheter assembly according to claim 1 wherein the balloon has an interior and wherein the guide wire tube extends into the interior of the balloon.

5. An intravascular catheter assembly according to claim 4 wherein the transitional member is secured to the guide wire tube at a location within the interior of the balloon.

6. An intravascular catheter assembly comprising:

a proximal shaft segment having a proximal end and a distal end;

a balloon;

a distal shaft segment connected between the distal end of the proximal shaft segment and the balloon, the distal shaft segment being more flexible than the proximal shaft segment;

the proximal shaft segment and the distal shaft segment having an inflation lumen defined therethrough to provide inflation pressure to the balloon;

a transition member secured to the proximal shaft segment and extending distally into the inflation lumen of the distal shaft segment;

a guide wire tube defining a guide wire lumen therethrough extending from a location proximal of the balloon to a location distal of the balloon;

a guide wire lumen inlet spaced distally from the distal end of the proximal shaft segment and communicating between the guide wire lumen and outside of the catheter; and a guide wire, the guide wire being inserted through the guide wire tube and guide wire lumen inlet.

7. An intravascular catheter assembly according to claim 6 wherein the transition member is less rigid than the proximal shaft segment.

8. An intravascular catheter assembly according to claim 6 wherein the proximal shaft segment is defined by a metallic tube.

9. An intravascular catheter assembly according to claim 6 wherein the distal shaft segment is made from a plastic material.

10. An intravascular catheter assembly according to claim 6 wherein the balloon has an interior and wherein the guide wire tube extends into the interior of the balloon.

11. An intravascular catheter assembly according to claim 10 wherein the transitional member is secured to the guide wire tube at a location within the interior of the balloon.

* * * * *